United States Patent
Vijverberg et al.

(10) Patent No.: US 6,776,119 B2
(45) Date of Patent: Aug. 17, 2004

(54) DEVICE AND METHOD FOR SEPARATING MILK FROM DAIRY ANIMALS

(75) Inventors: Helena Geralda Maria Vijverberg, Maassluis (NL); Elena Espada Aventin, Delft (NL)

(73) Assignee: Lely Enterprises A.G., Zug (CH)

(*) Notice: Subject to any disclaimer, the term of this patent is extended or adjusted under 35 U.S.C. 154(b) by 0 days.

(21) Appl. No.: 10/255,174

(22) Filed: Sep. 26, 2002

(65) Prior Publication Data

US 2003/0061992 A1 Apr. 3, 2003

(30) Foreign Application Priority Data

Sep. 28, 2001 (NL) .............................................. 1019059

(51) Int. Cl.$^7$ .............................................. A01J 5/007
(52) U.S. Cl. ................................................... 119/14.14
(58) Field of Search .......................... 119/14.15, 14.02, 119/14.08, 14.14, 14.18

(56) References Cited

U.S. PATENT DOCUMENTS

| | | | | |
|---|---|---|---|---|
| 4,190,020 A | * | 2/1980 | Tamas et al. ............ | 119/14.08 |
| 5,152,246 A | | 10/1992 | Wakui | |
| 5,275,124 A | * | 1/1994 | van der Lely et al. .... | 119/14.08 |
| 5,416,417 A | | 5/1995 | Peles | |
| 5,704,311 A | * | 1/1998 | van den Berg .......... | 119/14.02 |
| 5,873,323 A | * | 2/1999 | van den Berg et al. ... | 119/14.02 |
| 6,038,030 A | * | 3/2000 | van den Berg ............. | 356/425 |
| 6,493,071 B2 | * | 12/2002 | van den Berg et al. ....... | 356/72 |

FOREIGN PATENT DOCUMENTS

| | | |
|---|---|---|
| EP | 1 000 535 A1 | 5/2000 |
| WO | WO 97/47187 A1 | 12/1997 |
| WO | WO 99/31965 A1 | 7/1999 |

* cited by examiner

*Primary Examiner*—Charles T. Jordan
*Assistant Examiner*—Kimberly S. Smith
(74) *Attorney, Agent, or Firm*—Howrey Simon Arnold & White L.L.P.; Jacobus C. Rasser; David P. Owen

(57) ABSTRACT

A device for separating milk obtained from a dairy animal. Said device is provided with a processing device, with a measuring device for measuring at least one milk variable during a milking run of a dairy animal and for issuing a signal indicative of the measured value to the processing device. The processing device is provided with a memory suitable for containing a reference value for the milk variable, and with a comparing device for comparing the measured value of the milk variable with the reference value and for issuing a comparison signal. The device separates milk in dependence on the comparison signal. The measuring device is suitable for measuring during the entire course of the milking run the value of the milk variable for obtaining a momentary measurement pattern of the milk variable. The memory of the processing device is suitable for containing a reference measurement pattern, and the comparing device is suitable for comparing the momentary measurement pattern of a milk variable with the reference measurement pattern of the milk variable and for issuing a comparison signal indicative of the comparison result.

22 Claims, 3 Drawing Sheets

| | | |
|---|---|---|
| Colour Pattern (Blue) | COW 1. |  |
| | COW 2. |  |
| | COW 3. |  |
| | COW 4. |  |
| | COW 5. |  |
| | COW 6. |  |
| Conductivity Pattern | COW 7. |  |
| | COW 8. |  |
| | COW 9. |  |
| | COW 10. |  |
| | COW 11. |  |

DEVICE AND METHOD FOR SEPARATING MILK FROM DAIRY ANIMALS

CROSS REFERENCE TO RELATED APPLICATIONS

This application claims priority from the Netherlands application number 1019059 filed on Sep. 28, 2001, the contents of which are hereby incorporated by reference in their entirety.

BACKGROUND OF THE INVENTION

1. Field of the Invention

The present invention relates to devices and methods for separating milk from dairy animals. In this context, separating is used to refer to accepting or rejecting, or sorting milk according to particular criteria.

2. Description of the Related Art

Such a device is known from EP-A-1000535. The device known therefrom is provided with a measuring device in the form of a color measuring system provided with one or more sensors comprising one or more sources irradiating the milk successively or simultaneously with radiation of one or more different wavelengths and/or different intensities, while, during at least a part of the time when the sources are in their switched-on position, one or more receivers establish the radiation intensity during a time interval. When the obtained measurement data indicate that the color of the measured milk deviates from normal values, the relevant milk is separated. However, it has appeared that the known device sometimes draws a wrong conclusion on the basis of the color measurements, so that e.g. suitable milk is not used for being processed further, but is discharged.

BRIEF SUMMARY OF THE INVENTION

It is therefore desirable to provide an improved device for separating milk from a dairy animal by means of which the decision whether or not milk obtained is suitable for being processed further can be taken in an accurate manner.

According to the present invention, a device of the above-described type is provided for separating milk obtained from a dairy animal during a milking run. The device comprises a measuring device for measuring at least one milk variable during the course of the milking run of a dairy animal for obtaining a momentary measurement pattern of the milk variable and for issuing a signal indicative of the momentary measurement pattern. The device also includes a processing device for receiving the signal indicative of the momentary measurement pattern, the processing device comprising a memory for storing a reference measurement pattern for the milk variable and a comparing device for comparing the momentary measurement pattern of the milk variable with the reference measurement pattern and for issuing a comparison signal indicative of the comparison result.

By using not only a certain value, but the entire pattern i.e. course of the variable during the milking run for determining whether or not milk obtained should be processed further, it is possible to take a still more accurate decision whether or not the milk obtained should be processed further. Comparing measurement patterns with reference patterns appears to result in more correct decisions than exclusively comparing one single measured value.

In an embodiment of a device according to the, invention the processing device is provided with a memory for storing the measurement pattern respectively the reference measurement pattern.

The processing device is in particular provided with an averaging device for determining the average measurement pattern of a milk variable, it being advantageous that the memory is suitable for storing the average measurement pattern. Such an average measurement pattern is extremely useful for determining deviations from this average pattern, which may be an indication that the condition of the dairy animal is different from normal or that the milk produced by the dairy animal is different from normal. In other words the average measurement pattern constitutes the reference pattern. Such an average measurement pattern appears to provide per animal a more accurate indication of the deviation than a predetermined reference value. Especially when the average is a so-called progressive average, i.e. an average over e.g. the last ten milking runs (another number is possible as well), it is possible to make a correct decision.

Although for all the animals in a herd, the same thresholds may be used, it is advantageous that a memory of the processing device contains an upper threshold pattern and/or a lower threshold pattern for a relevant measurement pattern of a milk variable for each animal.

In a further embodiment of a device according to the invention, the device is provided with a milk line system comprising a number of lines and with at least one device controlled by the comparison signal for guiding milk flowing through the milk line system to a relevant line, it is possible to discharge automatically unsuitable milk or to convey suitable milk for being processed further.

For the purpose of enabling visual checking it is advantageous that the device comprises a displaying device for displaying the comparison signal. By providing the device with a device for generating a warning, said warning device being controlled by the comparison signal, it is possible, in certain situations, to give a warning to the manager of the device, e.g. in the form of a sound signal.

The measuring device preferably comprises a color sensor measuring system for measuring the intensity of at least one wavelength band, in particular in the visible wavelength range, of the milk obtained from the dairy animal, the variable being the intensity of the wavelength band. With the aid of the color sensor measuring system especially the intensity of the separate colors in the milk obtained from the separate udder quarters is established. Therefore, in this embodiment the variable is constituted by the color of the milk obtained.

In an embodiment of a device according to the invention the measuring device is constituted by a flow sensor for measuring the flow of the milk obtained during the milking run. The flow sensor preferably measures the flow of the milk obtained from the separate udder quarters.

In a further embodiment of a device according to the invention the measuring device is constituted by a conductivity meter known per se for measuring the conductivity of the milk obtained during the milking run. The conductivity meter preferably measures the conductivity of the milk obtained from the separate udder quarters.

In a still further embodiment of a device according to the invention the measuring device is constituted by a thermometer for measuring the temperature of the milk obtained during the milking run. The thermometer preferably measures the temperature of the milk obtained from the separate udder quarters.

In another further embodiment of a device according to the invention the measuring device is constituted by a component meter for measuring the quantity of a component of the milk obtained during the milking run, such as fat, protein, urea, bacteria, sugars, free fatty acids, germs, etc. The component meter preferably measures the components of the milk obtained from the separate udder quarters.

In a further embodiment of a device according to the invention the device is provided with a means for determining the period between two successive milking runs of the dairy animal, and the memory is suitable for containing a reference pattern depending on the measured period, respectively an upper threshold pattern and/or a lower threshold pattern depending on the measured period. This embodiment of the invention is based on the insight that the measured value of the variable depends on the measured period, also called interval, even when the condition of the dairy animal remains unchanged. By including, according to the invention, various reference values for the variable in the memory, the reference values depending on the measured period, a more accurate comparison of the measured values can take place, so that it is possible to take a correct decision whether or not the milk is suitable for being processed further. Moreover, after comparison of the measured values with the reference values, it is possible to draw more correct conclusions in relation to the condition respectively the health of the dairy animal. According to the invention, by period is meant in particular a period of time measured by a clock between two successive milking runs or a number of dairy animals milked between the two successive milking runs, said number being counted by a counter. Furthermore, another time-dependent variable may be measured as well, e.g. the total quantity of milk produced between the two successive milking runs.

The invention also includes a method for separating milk obtained from a dairy animal during a milking run. The method includes the steps of measuring a value of a variable in relation to the dairy animal during the entire course of the milking run, generating a momentary measurement pattern of the milk variable on the basis of the measured values, comparing the momentary measurement pattern with a reference measurement pattern for the milk variable, and separating milk based on the results of the comparison.

BRIEF DESCRIPTION OF THE DRAWINGS

The invention will be explained hereinafter in further detail with reference to an embodiment shown in the drawings, in which.

DESCRIPTION OF ILLUSTRATIVE EMBODIMENTS

Figure 1:
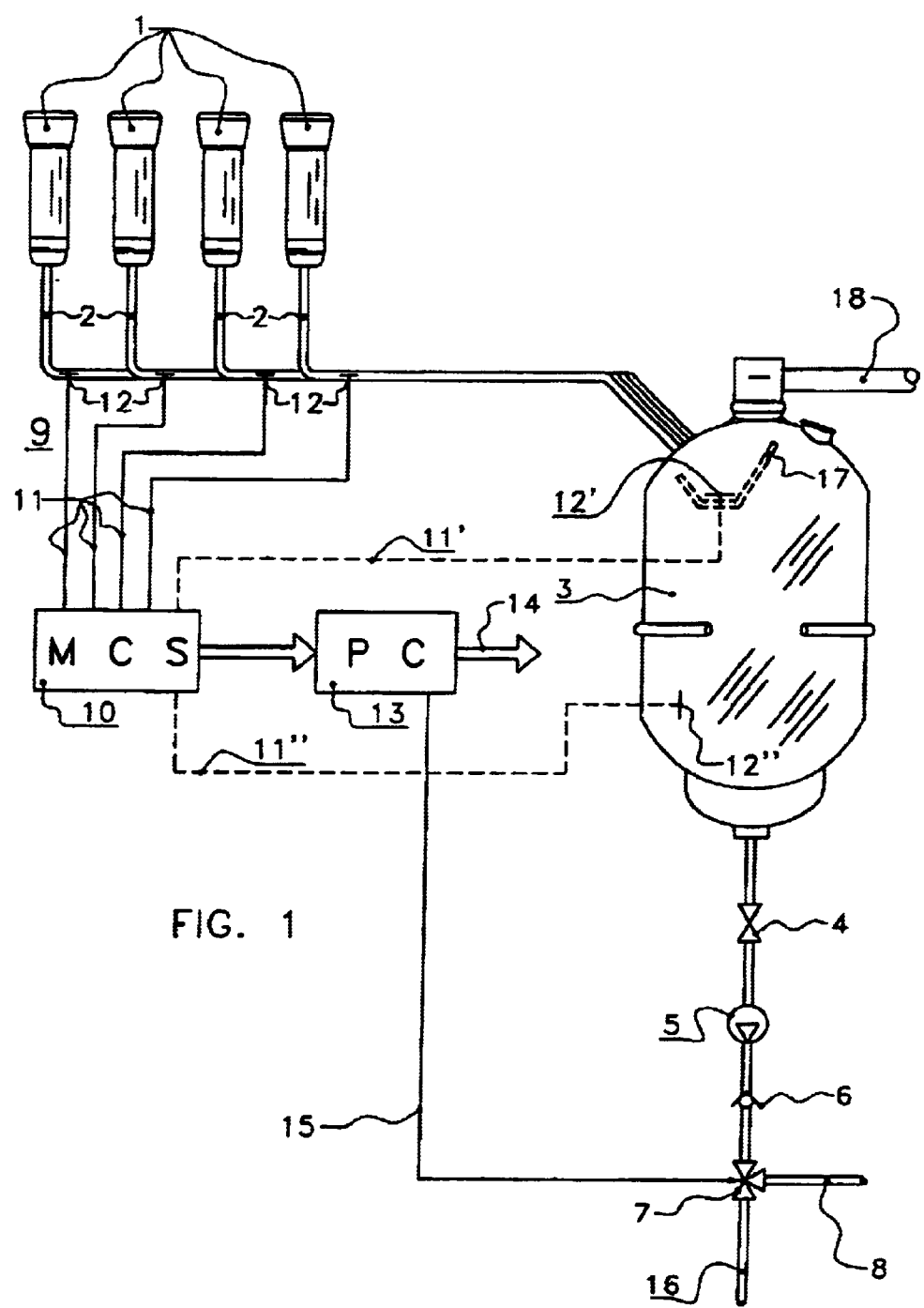
FIG. 1 is a schematic view of a device for milking a cow, provided with a color sensor measuring system.

FIG. 1 illustrates a device for milking a cow according to the present invention. Another application Ser. No. 10/255,173 based on Netherlands application No. 1019060 and filed concurrently herewith relates to similar subject matter, the contents of which are hereby incorporated by reference in their entirety.

FIG. 1 shows four teat cups 1 to be connected to the teats of an animal to be milked, the milk discharge lines 2 of said teat cups 1 opening into a milk glass 3. To the milk glass 3 there is further connected a vacuum line 18 for the purpose of applying a vacuum in the milk glass 3 itself, in the milk discharge lines 2 and in the teat cups 1, said vacuum being required for keeping the teat cups connected to the teats of the animal, for enabling milking and for separating milk and air present therein from each other in the milk glass 3. From the milk glass 3 the milk obtained is discharged via a valve 4, a pump 5, a non-return valve 6 and a three-way valve 7 through a line 8 to a not further shown milk tank.

FIG. 1 further shows a color sensor measuring system 9, said measuring system comprising a color intensity processing unit (MCS) 10, to which four sensors 12 are connected via glass fibre cables 11. Said sensors 12 are disposed in the milk lines 2 for establishing the intensity of a number of defined colors in the milk and for supplying signals representing these intensities to the processing unit 10. As a color sensor measuring system may be used the Modular Color Sensor system CS1 of Stracon Messsysteme GmbH, Im Camisch 10, Kahla. The sensors used in this system are sensitive to frequencies in frequency bands for red (R), green (G) and blue (B). Therefore there are issued three signals per measurement, which may be considered as intensity values for these three colors.

Although until now the opinion prevailed that for milk of a constant composition these three intensity values have a fixed mutual relation, said relation depending i.e. on the impurities and components in the milk, it has appeared that for certain dairy animals the relation between the three intensity values depends on the interval, in other words depends on the period between two successive milking runs. The period appears to be in particular a period of time between the two successive milking runs, but alternatively there appears to be a relation between the number of cows milked respectively the quantity of milk produced and the intensity values.

The color intensity processing unit (MCS) 10 comprises a computer (PC) 13 (shown in the figure separately from the color intensity processing unit (MCS) for the sake of clarity), in which for each animal to be milked there is a file in which all data required for milking a relevant animal are stored.

During the entire course of a milking run also the obtained three intensity values of the relevant colors in the milk are stored. These intensity values stored at each milking run thus constitute a color measurement pattern. The progressive average may be determined from the color measurement patterns obtained for a certain animal during a defined number (e.g. ten, but another number is possible as well) of the last milking runs carried out. Upon averaging preferably milking runs with equal intervals are used. The color patterns obtained at a next milking run with an equal interval may be compared with this progressive average color measurement pattern, i.e. the last obtained color measurement pattern of each of the three colors may be compared with the corresponding color measurement pattern (preferably belonging to the same interval), recorded in the computer as a progressive average. In other words, the color measurement patterns are compared both mutually and with corresponding color measurement patterns recorded during one or more previous milking runs (preferably with an equal interval). This comparison process takes place in the computer 13 which also functions as a comparing device. Subsequently the results of this comparison process may be displayed on a displaying device in such a manner that the presence of certain substances, such as impurities, in the milk can be read directly therefrom. These results may be supplied via the line 14 to a screen or to a printer.

Instead of determining the progressive average of the color measurement pattern for each of the colors, it is also possible to determine in another manner for each color a calibration pattern, such as in particular a reference pattern, respectively a lower threshold pattern or an upper threshold pattern. It is possible to apply calibration patterns which could hold for the milk obtained from all the animals or from a group of animals. In that case it will not be necessary to dispose a sensor 12 in each of the milk discharge lines 2, but an overflow reservoir 17 may be disposed in the milk glass 3, in which overflow reservoir there is provided such a sensor 12' which is connected to the processing unit 10 via a glass fibre cable shown by a "dashed" line 11'. As a further alternative a sensor 12" may be disposed in the lower part of the milk glass 3. Also in the latter case said sensor has to be connected to the processing unit 10 via a glass fibre cable 11".

However, in all situations it applies that, when inadmissible quantities of undesired substances appear to be present in the milk, the computer 13 issues a signal over the line 15 to the three-way valve 7, via which three-way valve 7 and the discharge line 16 connected thereto the milk containing these undesired substances may be discharged separately.

When for example blood has come into the milk, the color measurement pattern issued by the sensor 12 for the color red, will be a different pattern than when no blood is present in the milk. This color measurement pattern will then be higher than the color measurement pattern established on the basis of the progressive average or higher than the calibration pattern applied (preferably in dependence on the comparison with patterns belonging to the same interval). Also when there are no impurities in the milk, alterations in the concentration of substances normally being present in the milk may still be established.

It has further appeared that the color measurement patterns for the three colors have a different mutual ratio for different animals. Therefore it is advantageous to determine the color measurement patterns for each animal separately at each milking run and to compare them with calibration patterns or, in particular, with progressive average color measurement patterns established for this specific animal (and preferably belonging to the same interval).

An example of the dependence of the measured color intensity (and consequently of the measured color pattern) on the interval, said dependence having been proved clearly by means of the above-mentioned color sensor measuring system, is given hereinafter. It has further appeared that this dependence is reproducible. For a particular cow it has appeared that the intensity of the blue frequency band rises in a particular manner when the period of time, the interval, increases and/or the number of cows having been milked and/or the quantity of milk produced increases. It has further appeared that the intensity of the green frequency band shows a certain, slight fall at an increasing interval. The intensity of the red frequency band showed a certain slight rise. For this cow the total sum of the intensities appeared to rise to a maximum value at an increasing interval and to fall via a particular pattern at a further increasing interval. The value of the intensity in the red frequency band reduced by the value of the blue frequency band appeared to show with this cow a falling pattern at an increasing interval, whereas the quotient of the intensity in the red frequency band and the intensity in the green frequency band rose to a maximum value at an increasing interval and remained constant at a further increase of the interval. It will be obvious that upon comparing the milk obtained from this cow, at each interval there has to be taken a different reference value or pattern to decide whether or not the milk obtained is suitable for being processed further.

It has further appeared that the color intensity may differ per quarter, so that it is advantageous to compare the color measurement pattern per animal, per quarter, and preferably per interval, in order to be able to decide whether or not milk obtained from a quarter should be processed further.

It has further appeared that the flow pattern of the milk obtained during the milking run differs per animal and further depends on the interval. Also here, to be able to take a correct decision whether or not the milk obtained should be processed further, the measured pattern of the flow has to be compared with a reference pattern for that interval. It is noticed that a flow sensor for measuring the flow of the milk obtained during the milking run is known per se. In particular the flow sensor measures the flow pattern of the milk obtained from the separate udder quarters.

It has further appeared that the conductivity pattern over the entire milking run may be different per animal or per group of animals, and may provide a more accurate decision whether or not the milk obtained should be processed further than only one single measured value. Besides, the conductivity of the milk obtained for the mentioned cow rises at an increasing interval. A conductivity meter for measuring the conductivity pattern of the milk obtained during the milking run, in particular per quarter, may then be used to take a correct decision whether or not the milk obtained (possibly per quarter) should be processed further.

It has further appeared that the temperature of the milk obtained for the mentioned cow rises at an increasing interval. In that situation a thermometer may be used for measuring the temperature pattern of the milk obtained during the milking run, in particular for measuring the temperature pattern of the milk obtained from the separate udder quarters, in order to take a correct decision whether or not the milk obtained (possibly per quarter and/or per interval) should be processed further.

Moreover it has appeared that for the mentioned cow the fat content of the milk obtained falls according to a certain curve at an increasing interval. Also for other components there appears to be a dependence between the quantity and the interval. A component meter for measuring the quantity pattern of a component of the milk obtained during the milking run, such as fat, protein, urea, bacteria, sugars, free fatty acids, germs, etc., in particular the component pattern of the milk obtained from the separate udder quarters, may then be used for taking a correct decision whether or not the milk obtained (possibly per quarter and/or per interval) should be processed further.

The above-mentioned relations have not only been found with a particular cow, but all cows appear to produce milk of which the measurable variables show a cow-dependent pattern. A certain pattern for one cow may then indicate milk suitable for being processed further, whereas the same pattern measured on milk obtained from another cow may indicate milk which is not suitable for being processed further.

As already mentioned above for color intensity measurement, according to the invention a measured measurement pattern (also called measured curve) of the variable is used to decide during the milking run whether or not milk obtained should be processed further. This applies in particular to the pattern of color, conductivity and flow during a milking run, although the other above-mentioned variables also show a pattern during the milking run, which pattern may be used for obtaining a correct decision whether or not milk obtained is suitable for being processed further.

Figure 3:
FIG. 3 shows a number of normal measurement patterns for particular cows.
Figure 3:
Figure 3:
Figure 3:
Figure 3:
Figure 3:
Figure 3:
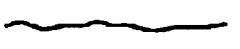
Figure 3:
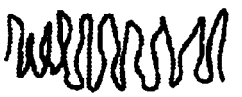
Figure 3:
Figure 3:
Figure 3:
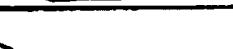

Examples of normal measurement patterns measured with different dairy animals in relation to color and conductivity, which normal measurement patterns indicate milk suitable for being processed further, are shown in FIG. 3.

Such a normal measurement pattern may be a predetermined measurement pattern, or an average measurement pattern for an animal (preferably per interval). To that end there is provided an averaging device for determining the average of a measurement pattern of a milk variable. Besides, other reference patterns may be used as well (for example an upper threshold pattern and/or lower threshold pattern).

Figure 2:
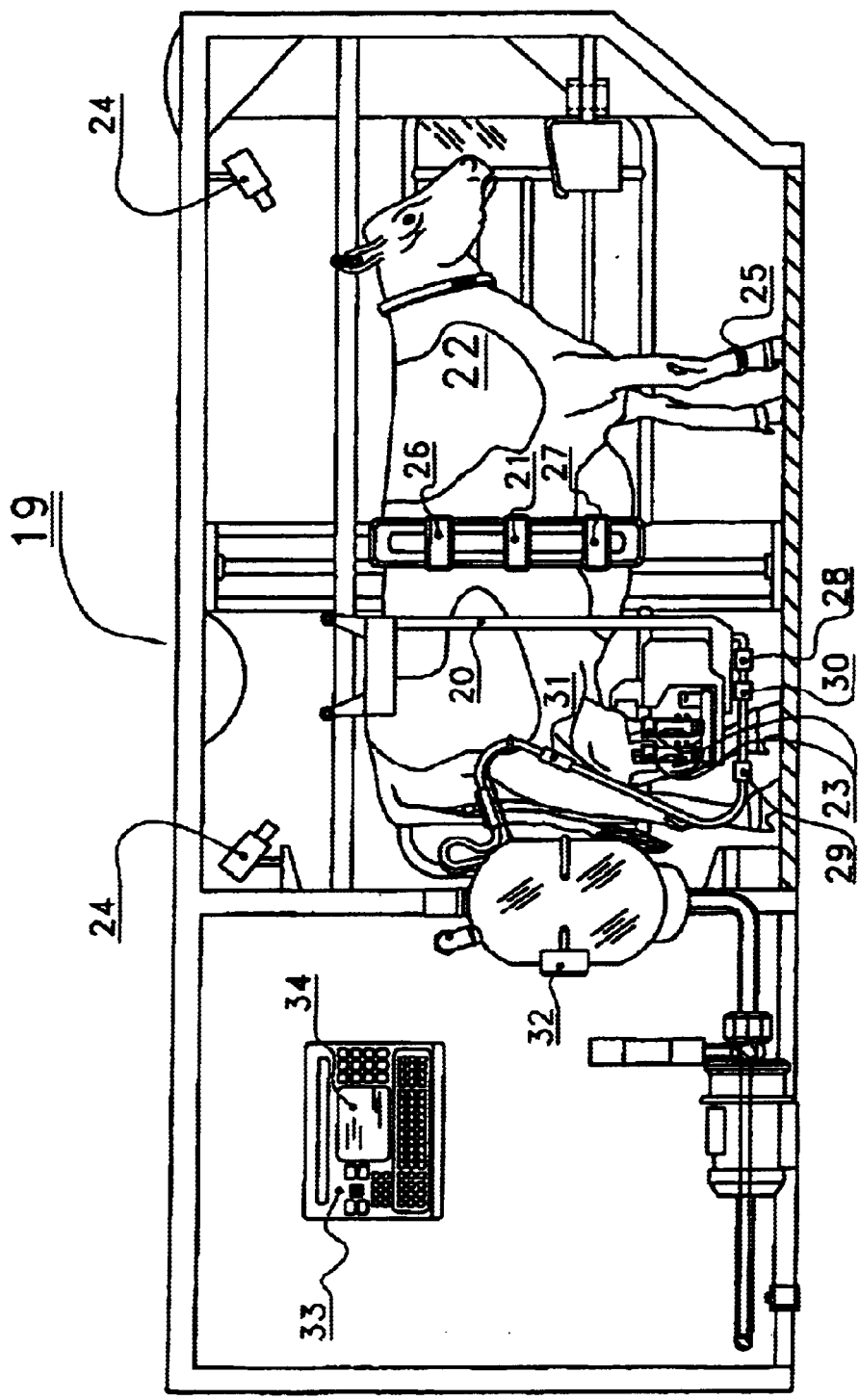
FIG. 2 is a schematic view of a milking box with a milking robot provided with means for measuring a variable in relation to the cow.

FIG. 2 shows schematically a milking box 19 with a milking robot 20, to which the invention applies in particular. In this figure various measuring devices for measuring the pattern of the values of variables in relation to the cow are shown schematically.

For the purpose of measuring the health of the cow 22, further the heart beat is measured by means of a band 21 including a heart beat meter around the leg or the abdomen of the cow 22. Alternatively or additionally a heart beat meter known per se may be provided on the cow 22 near a place where an artery is located, in this connection the udder or an ear of the cow may be taken into consideration. A suitable heart monitoring system is for example obtainable at Polar Electro Oy, Helsinki, Finland. Alternatively a heart beat meter may be included in at least one of the teat cups 23.

In the milking box 19 there may be disposed one or more cameras 24 for observing and measuring the activity of the cow 22, which may also be used for monitoring the condition of health of the cow 22. The video pictures are analysed by movement recognition equipment known per se for determining activity parameters such as stepping, kicking and the like. To that end the picture is compared per cow 22 with stored historical data regarding the cow 22. There may further be provided a step counter 25, a muscle contraction meter 26 and/or a muscle vibration meter 27 for determining the activity of the cow 22. Besides, the milk yield is measured by a quantity meter 32 or yield meter.

A flow sensor 28 measures the flow pattern of the milk obtained during a milking run. A conductivity meter 29 measures the conductivity pattern of the milk obtained during a milking run. A thermometer 30 measures the temperature pattern of the milk obtained during a milking run. A component meter 31 measures the component quantity pattern, e.g. protein and fat, in the milk obtained during the milking run. All these measurement data are transmitted to or read by a processing device 33 comprising a computer having a memory. Besides the measurement data the processing device 33 preferably also stores the period of time elapsed since the same animal has been milked. Alternatively the number of cows milked or the quantity of milk produced is stored. To that end the processing device 33 comprises a clock (not explicitly shown, but implicitly present in the computer) for determining the period of time between two successive milking runs of the dairy animal. Alternatively there may be provided a counter for counting the number of cows milked or a meter for measuring the quantity of milk produced. In the memory of the computer of the processing device 33 reference patterns are stored per interval, per animal or per group of animals, possibly per quarter, and per milk variable, respectively these reference patterns are generated by the system itself. The processing device 33 comprises a (non-shown) comparing device for comparing the measured pattern of the variable with the stored reference patterns. The comparing device issues a comparison signal, the value of which depends on the comparison result, and is thus indicative of the comparison result. This comparison signal may be displayed on a displaying device, such as a screen 34. As described above, the comparison signal may also be used for controlling a valve or the like, so that the milk obtained will be processed further or not. Should the comparison signal indicate a deviation, then it is also possible for the comparison signal to control a device for generating a warning (such as e.g. a loudspeaker) for issuing a signal (e.g. a sound) which is perceptible by a manager of the device.

It will be obvious that the measurement patterns may be used separately, but that also combinations of measurement patterns of different variables may be used for determining whether or not milk should be processed further (or for determining whether the condition of a dairy animal is within the standards). Thus a weight factor may be given to certain parameters or comparison results may be given for combining the measurement patterns obtained in a desired manner.

As described, FIG. 2 shows a side view of a milking box 19 with a cow 22 present therein. The milking box 19 is provided with a milking robot 20 with teat cups 23 which are automatically connected to the teats of the cow 22 by means of the milking robot 20. Near the front side of the milking box 19 there is further disposed a feeding trough to which concentrate may be supplied in metered quantities. Other elements of the milking box and the robot are not shown in the figure for the sake of clarity.

Many modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A device for separating milk obtained from a dairy animal during a milking run, the device comprising:
   a measuring device for measuring at least one milk variable during an entire course of the milking run of the dairy animal for obtaining a momentary measurement pattern defining a variation of the milk variable during the milking run and for issuing a signal indicative of the momentary measurment pattern; and
   a processing device for receiving the signal indicative of the momentary measurement pattern, the processing device comprising:
   a memory for storing a reference measurement pattern for the milk variable; and
   a comparing device for comparing the momentary measurement pattern of the milk variable with the reference measurement pattern and for issuing a comparison signal indicative of the comparison result.

2. A device as claimed in claim 1, wherein the memory stores the momentary measurement pattern.

3. A device as claimed in claim 1, wherein the processing device further comprises an averaging device for determining an average measurement pattern of the milk variable.

4. A device as claimed in claim 3, wherein the memory stores the average measurement pattern.

5. A device as claimed in claim 1, wherein the memory stores an upper threshold pattern or a lower threshold pattern for the momentary measurement pattern of the milk variable of the dairy animal.

6. A device as claimed in claim 5, further comprising a milk line system comprising a plurality of lines and at least one device controlled by the comparison signal for guiding milk flowing through the milk line system to one of the lines.

7. A device as claimed in any claim 1, further comprising a displaying device for displaying the comparison signal.

8. A device as claimed in claim 1, further comprising a warning device for generating a warning, the warning device being controlled by the comparison signal.

9. A device as claimed in claim 1, wherein the measuring device comprises a color sensor measuring system for measuring intensity of at least one wavelength band of the milk obtained from the dairy animal, and wherein the variable is the intensity of the wavelength band.

10. A device as claimed in claim 9, wherein the color sensor measuring system provides information for determining intensity of the separate colors in the milk obtained from separate udder quarters of the dairy animal.

11. A device as claimed in claim 1, wherein the measuring device comprises a flow sensor for measuring a flow of the milk obtained during the milking run.

12. A device as claimed in claim 11, wherein the flow sensor measures the flow of the milk obtained from separate udder quarters of the dairy animal.

13. A device as claimed in claim 1, wherein the measuring device comprises a conductivity meter for measuring conductivity of the milk obtained during the milking run.

14. A device as claimed in claim 13, wherein the conductivity meter measures conductivity of the milk obtained from the separate udder quarters of the dairy animal.

15. A device as claimed in claim 1, wherein the measuring device comprise a thermometer for measuring temperature of the milk obtained during the milking run.

16. A device as claimed in claim 15, wherein the thermometer measures temperature of the milk obtained from the separate udder quarters of the dairy animal.

17. A device as claimed in claim 1, wherein the measuring device comprises a component meter for measuring a quantity of a component of the milk obtained during the milking run.

18. A device as claimed in claim 17, wherein the component meter measures the component of the milk obtained from the separate udder quarters of the dairy animal.

19. A device as claimed in claim 5, wherein the device determines a period since a preceding milking run of the dairy animal, and the memory stores a plurality of reference patterns and upper or lower threshold patterns dependent on the measured period.

20. A device as claimed in claim 19, wherein the device comprises a clock for measuring a period of time between two successive milking runs to determine the period since a preceding milking run of the dairy animal.

21. A device as claimed in claim 19, further comprising a counter for counting the number of dairy animals milked since a last milking run of the dairy animal to determine the period since a preceding milking run of the dairy animal.

22. A device for separating milk obtained from a dairy animal during a milking run, said device comprising:

measuring means for measuring at least one milk variable during the course of the milking run of a dairy animal for obtaining a momentary measurement pattern defining a variation of the milk variable during the milking run and for issuing a signal indicative of the momentary measurement pattern;

processing means for receiving the signal indicative of the momentary measurement pattern, the processing means comprising:

memory means for storing a reference measurement pattern for the milk variable; and means for comparing the momentary measurement pattern of the milk variable with the reference measurement pattern and for issuing a comparison signal indicative of the comparison result.

* * * * *